ent [19] [11] 3,971,382
Krasnov [45] July 27, 1976

[54] METHOD OF NON-SURGICAL TREATMENT OF CATARACTS

[76] Inventor: Mikhail Mikhailovich Krasnov, ulitsa Vesnina, 30, kv. 12, Moscow, U.S.S.R.

[22] Filed: Nov. 22, 1974

[21] Appl. No.: 526,311

Related U.S. Application Data

[63] Continuation of Ser. No. 423,749, Dec. 11, 1973, abandoned.

[52] U.S. Cl. .............................................. 128/303.1
[51] Int. Cl.² ......................................... A61B 17/36
[58] Field of Search ................ 128/303.1, 395, 2 R; 331/94.5

[56] References Cited

UNITED STATES PATENTS

| | | | |
|---|---|---|---|
| 3,481,340 | 12/1969 | McKnight et al. | 128/395 |
| 3,710,798 | 1/1973 | Bredemeier | 128/303.1 |
| 3,769,963 | 11/1973 | Goldman et al. | 128/303.1 |
| 3,809,092 | 5/1974 | Abraham | 128/395 |

OTHER PUBLICATIONS

V. Cohn, Washington Post, Apr. 5, 1973, pp. A1, A6.

Primary Examiner—Lawrence W. Trapp
Attorney, Agent, or Firm—Holman & Stern

[57] ABSTRACT

A method of non-surgical treatment of soft and membraneous cataracts, including congenital cataracts, said method comprising the step of cutting the anterior capsule of the lens and/or pupillary membrane without perforating injury to the eye wall with a laser beam, caused to pass through the cornea, the anterior chamber of the eye and pupil, and then be focused onto the anterior capsule of the lens and/or pupillary membrane to thus form at least one hole through which the cataract substance is thus let out of the lens capsule/soft cataract/into the anterior chamber of the eye where the substance is gradually dissolved.

5 Claims, No Drawings

METHOD OF NON-SURGICAL TREATMENT OF CATARACTS

This is a continuation of application Ser. No. 423,749, filed Dec. 11, 1973, now abandoned.

BACKGROUND OF THE INVENTION

The present invention relates to the application of a laser beam for cataract treatment, and more particularly to the laser treatment of the soft and membranous types of cataract found in young patients, including congenital cataracts.

In adults, when a hard nucleous is formed inside the lens, the present method is not indicated.

In soft cataracts, a small cut of the lens capsule is sufficient to let the cataract substance out of the lens capsule into anterior chamber of the eye, where the substance is gradually dissolved.

In membranous cataracts, cutting of the pupillary membrane (the so-called discission procedure) is in itself a preferred treatment.

To date, surgery is the only known way to produce the said cut in the lens capsule and/or pupillary membrane.

This technique has disadvantages in that it involves all the dangers inherent to surgery.

Among such dangers are: a perforating injury to the eye, would cause leakage the distulization cicatrix of cornea tissue profileration development of synechias in the anterior chamber, the possibility of infection and inflammation and other complications.

SUMMARY OF THE INVENTION

Accordingly, it is an object of the present invention to provide a method that will ensure cutting of the anterior capsule of the lens and/or pupillary membrane without surgery and without a perforating injury to the eye.

The method of the invention is thus free of all the disadvantages of known techniques.

A further object of the invention is the provision of a painless cutting of the anterior capsule of the lens and/or pupillary membrane.

Still another object is to provide a simple and quick method.

Still another object of the present invention is to provide a simple way to cut the anterior capsule of the lens and/or pupillary membrane in an out-patient basis when hospitalization is not necessary.

DESCRIPTION OF A PREFERRED EMBODIMENT

Additional objects and advantages of the invention will be set forth in part in the description which follows, and in part such objects and advantages will be obvious from the description, or may be learned by the practice of the invention.

The objects and advantages are realized and attained by the devices and methods particularly set forth out in the appended claims.

To achieve these and other objects, the present invention provides a method of non-surgical treatment of cataracts wherein a cut in the anterior capsule of the lens and/or pupillary membrane is made by a laser beam, the beam passing through the cornea, the anterior chamber of the eye and the pupil to be focused upon the anterior capsule of the lens and/or pupillary membrane, thus ensuring the cutting of the capsule.

The cataract substance is thus let out into the anterior chamber of the eye where the substance is gradually dissolved.

As here embodied, the present method preferably includes utilisation of a Q-switched pulsed laser beam.

It is to be understood, of course, that both the foregoing general description and the following detailed description are explanatory only and are not restrictive of the invention.

To perform the method a laser unit such as described in our copending patent application to the U.S. patent office Ser. No. 308,936, filed on Nov. 24, 1972 is contemplated to be used.

Yet, other types of laser units having the same output parameters are also suitable to perform the method.

The laser unit is adapted to a standard device comprising a slit lamp or operating microscope to ensure exact aiming and focusing of the laser beam on the plane of the lens capsule and the performing of the cutting.

Adapting the laser unit to a conventional slit lamp proved to be most convenient.

The inventive method does not require any special preparation or anesthesia (except of a conventional topical anesthetic, for example, drops of pontocain).

Treatment may be carried out in a sitting position of the patient.

The laser beam is focused into a spot of 0.1 to 0.7 mm in diameter on the anterior portion of the lens capsule and/or pupillary membrane.

One or more pulses are made to make a hole or several holes of the required size.

According to the results of our investigations, certain kinds of laser irradiation are most suitable and serve the desired purpose best.

These are Q-switched laser pulses with a wavelength from 5300 to 10600 A, the pulse duration being from $10^{-7}$ to $10^{-12}$ sec, and the power output being from $10^7$ to $10^9$ w.

The invention method has been experimentally tested on the eyes of chinchilla rabbits.

Eighteen cataract patients have so far been treated. No complications were noted within a period of one year and a half.

Mystological studies (our patent application Ser. No. 308,936 filed Nov. 24, 1972) performed with the same laser unit within the same ranges of wavelength, power and time also proved full safety to the eye.

In all patients, cataract substance dissolved in 10 weeks to 1 year after the procedure.

The invention in its broader aspects is not limited to the specific details described and departures may be made from such details without departing from the principles of the invention and without sacrificing its chief advantages.

What is claimed is:

1. A method of non-surgical treatment of soft and membraneous cataracts, including congenital cataracts, said method comprising the step of cutting the anterior capsule of the lens and/or pupillary membrane without perforating injury to the eye wall with a laser beam caused to pass through the cornea, the anterior chamber of the eye and the pupil, and then be focused onto the anterior capsule of the lens and/or pupillary membrane to thus form at least one hole through which the cataract substance is thus let out of the lens capsule/soft cataract/into the anterior chamber of the eye where the substance is gradually dissolved.

2. A method of non-surgical treatment of cataracts as in claim 1, wherein the laser beam is produced by a pulsed Q-switched laser.

3. A method of non-surgical treatment of cataracts as in claim 1 wherein the laser beam is focused into a spot with diameter of 0.2 – 0.5 mm.

4. A method of non-surgical treatment of cataracts as in claim 1 wherein the wavelength of the laser irradiation is of 5 300 A to 10 600 A.

5. A method of non-surgical treatment of cataracts as in claim 1, wherein the laser is pulsed at least once.

* * * * *